United States Patent [19]

Harandi et al.

[11] Patent Number: 5,113,024
[45] Date of Patent: May 12, 1992

[54] PROCESS FOR PRODUCT SEPARATION IN THE PRODUCTION OF DI-ISOPROPYL ETHER

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 711,768

[22] Filed: Jun. 7, 1991

[51] Int. Cl.$^5$ .................. C07C 41/05; C07C 41/38
[52] U.S. Cl. .................. 568/697; 568/694; 568/699
[58] Field of Search .................. 568/694, 697, 699

[56] References Cited

U.S. PATENT DOCUMENTS

| 4,214,107 | 7/1980 | Chang | 568/897 |
| 4,857,664 | 8/1989 | Huang | 568/695 |
| 4,906,787 | 3/1990 | Huang | 568/697 |
| 4,981,491 | 1/1991 | Harandi et al. | 568/697 |
| 5,011,506 | 4/1991 | Harandi et al. | 568/697 |

Primary Examiner—Marianne Cintins
Assistant Examiner—John D. Peabody, III
Attorney, Agent, or Firm—Alexander J. McKillop; Charles J. Speciale; L. G. Wise

[57] ABSTRACT

In the instant invention the effluent from the DIPE reactor is separated in a novel separation process that includes, in one embodiment, two extraction steps serially combined to initially separate IPA from the reaction products by extraction with water. The aqueous IPA extract is separated in a second extraction step carried out using the $C_3$ hydrocarbon feedstream to the process as extractor. To effectuate the separation of aqueous IPA, the second extraction is carried out at a temperature higher than that of the first extraction step. The organic phase from the first extraction containing DIPE, $C_3$ hydrocarbons and water is separated in a splitter to provide dry DIPE as product. In another embodiment dry DIPE is produced by an initial aqueous extraction of the reaction effluent followed by distillation to separate $C_3$ hydrocarbons and water overhead and DIPE as a bottom stream.

14 Claims, 1 Drawing Sheet

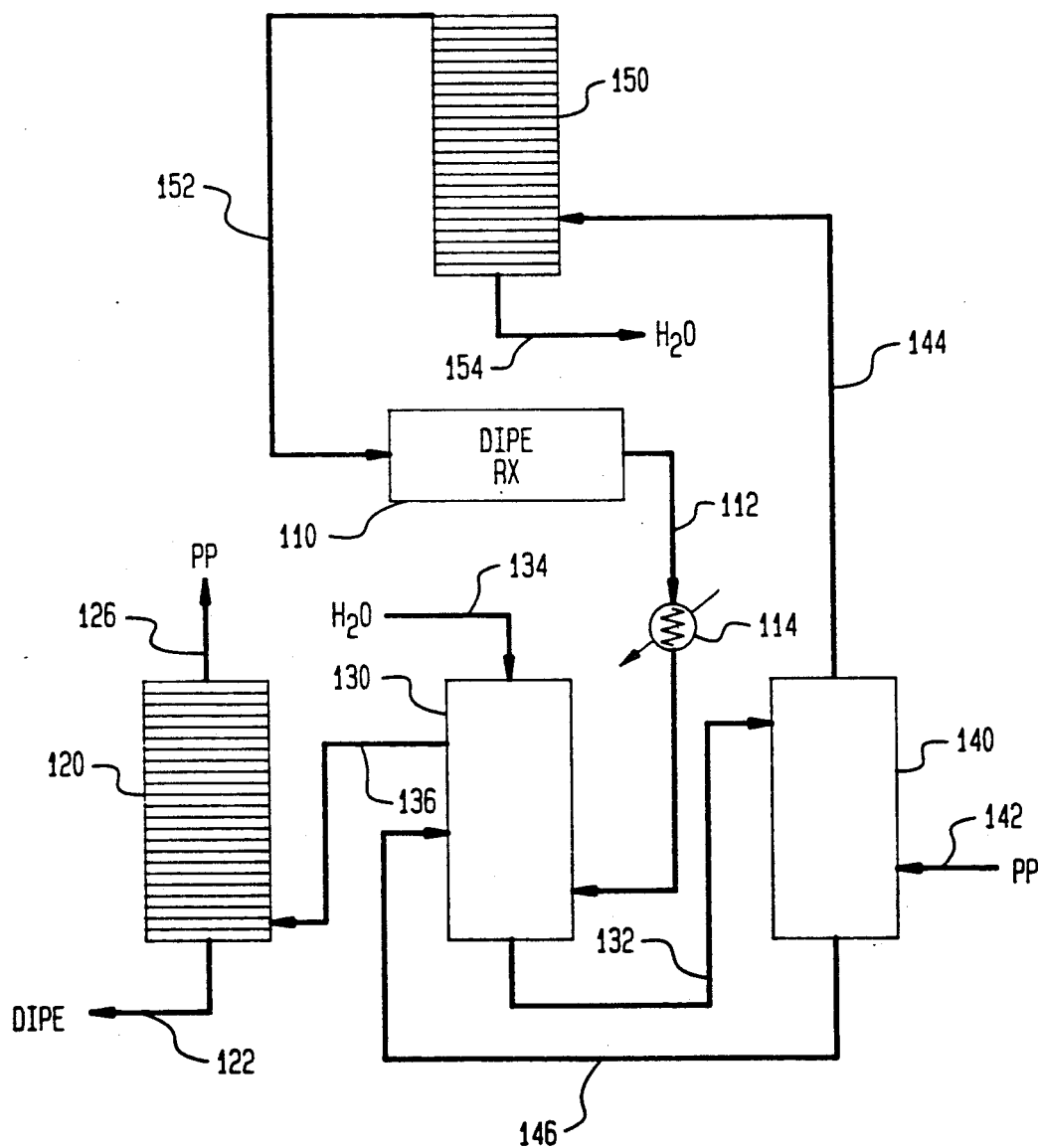
FIG.

PROCESS FOR PRODUCT SEPARATION IN THE PRODUCTION OF DI-ISOPROPYL ETHER

This invention relates to processes for the production of diisopropyl ether. More particularly, the invention relates to novel improvements in the downstream product recovery operations for DIPE that reduce the requirement for the separation of isopropyl alcohol by distillation. Product recovery is accomplished by a combination of extraction and distillation operations that effectively separate water, diisopropyl ether (DIPE) and isopropanol (IPA).

BACKGROUND OF THE INVENTION

Lower molecular weight alcohols and ethers such as isopropanol (IPA) and diisopropyl ether (DIPE) are in the gasoline boiling range and are known to have high blending octane numbers. In addition, by-product propylene from which IPA and DIPE can be made is usually available in a fuels refinery. An important aspect of research in the petroleum industry relates to processes to produce high octane lower aliphatic alkyl ethers as octane boosters and supplementary fuels.

The catalytic hydration of olefins, particularly $C_3$ and $C_4$ olefins, to provide alcohols and ethers is a well-established art. Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, among others.

The production of ether from secondary alcohols such as isopropanol and light olefins is known. As disclosed in U.S. Pat. No. 4,182,914, DIPE is produced from IPA and propylene in a series of operations employing a strongly acidic cation exchange resin as catalyst. Recently, processes for the hydration of olefins to provide alcohols and ethers using zeolite catalyst have been disclosed by Bell et el. in U.S. patent applications Ser. Nos. 414,630 filed Sep. 26, 1989 now abandoned; 427,926 filed Oct. 25, 1989 now abandoned) and U.S. Pat. Nos. 4,214,107 and 4,499,313 to Bell et al.; and U.S. Pat. No. 4,757,664, 4,857,664 and 4,906,187 to T. Huang. These applications and patents are incorporated herein in their entirety by reference.

In the conversion of a water feedstream and a $C_3$ hydrocarbons feedstream comprising propene and propane to DIPE and IPA as conventionally practiced, the conversion per pass is about 60%. The reaction effluent is a mixture containing unreacted water, $C_3$ hydrocarbons and hydrocarbon oligomeric by-products, in addition to the DIPE and IPA products. Separating these components requires multiple distillation and extraction operations that represent a substantial part of the overall process costs. $C_3$ and any lower hydrocarbons present are effectively removed by distillation. However, separation of DIPE and IPA is accomplished by an aqueous extraction operation that requires a further distillation step to separate alcohol and water. This extraction and distillation of IPA from the reaction effluent in order to recycle IPA to the etherification reactor as typically carried out imposes an inordinate cost burden on the process in view of the formation of an IPA-water azeotrope which affects the complexity of the distillation tower design and operation. The discovery of new methods to overcome the complexity of the IPA-water distillation operation represents a continuing challenge to artisans in the field.

It is an object of the present invention to provide a process for the production of diisopropyl ether at lower overall process cost and complexity.

It is another object of the present invention to provide an improved process for the steps of product separation of IPA and water in downstream DIPE operations.

Another object of the present invention is to reduce the requirements for IPA-water distillation step in DIPE product separation.

A further object of the invention is to provide a means to utilize hydrocarbon feedstock to separate IPA-water by extraction in DIPE production.

SUMMARY OF THE INVENTION

It has been discovered that the process to produce diisopropyl ether and the distillation step for the separation of aqueous IPA recovered from the DIPE extraction operations can be modified to reduce the costly distillation of the isopropanol-water azeotrope derived from the aqueous extraction of the reaction products and improve the overall process thereby. In the instant invention the effluent from the DIPE reactor is separated in a novel separation process that includes two extraction steps serially combined to initially separate IPA from the reaction products by extraction with water. The aqueous IPA extract is separated in a second extraction step carried out using the $C_3$ hydrocarbon feedstream to the process as extractor to separate a major portion of IPA in the aqueous IPA extract. To effectuate the separation of aqueous IPA, the second extraction is carried out at a temperature higher than that of the first extraction step. The organic phase from the second extraction step, containing IPA, water and $C_3$ hydrocarbons, is further separated by distillation to provide the feedstream to the DIPE reactor.

More particularly, a process has been discovered for the production of diisopropyl ether comprising a) contacting a feedstream comprising $C_3$ hydrocarbons, isopropanol and water with acidic olefin hydration and etherification catalyst under etherification conditions at elevated pressure in an etherification zone to produce an effluent stream containing diisopropyl ether, isopropanol, unreacted water, unreacted $C_3$ hydrocarbons and higher olefinic hydrocarbons.

The effluent is extracted with water in a first extraction zone to produce a first organic phase containing diisopropyl ether and unreacted $C_3$ hydrocarbons and a first aqueous phase comprising isopropanol and water. The aqueous IPA phase is extracted with fresh $C_3$ hydrocarbon feedstock rich in propene in a second extraction zone to produce a second aqueous phase containing a minor portion of isopropanol and a second extraction organic phase comprising $C_3$ hydrocarbons, a major portion of isopropanol and water. The second extraction organic phase is fractionated to provide the feedstream to the etherification zone.

The present invention further includes a novel reactor system for the production of diisopropyl ether, comprising in combination: a reactor means for contacting a feedstream comprising $C_3$ hydrocarbons, isopropanol and water with acidic olefin hydration and etherification catalyst under etherification conditions at elevated pressure in an etherification zone to produce an effluent stream containing diisopropyl ether, isopropanol, unreacted water, unreacted $C_3$ hydrocarbons and higher olefinic hydrocarbons; a first extractor means for separating the effluent stream with water in a first extraction zone to produce a first organic phase containing diisopropyl ether and unreacted $C_3$ hydrocarbons and a first aqueous phase comprising isopropanol and water; a second extractor means for extracting the first aqueous phase with fresh $C_3$ hydrocarbon feedstock rich in propene in a second extraction zone to produce a second aqueous phase containing isopropanol and a second extraction organic phase; fractionator means receivably connected to said second extractor for separating the second organic phase; and means, operably connected to an upper portion of said fractionator and to said reactor means, for transferring fractionator overhead stream to said reactor means.

DESCRIPTION OF THE FIGURES

The Figure is a schematic process flow diagram of the process of the instant invention.

DETAILED DESCRIPTION OF THE PROCESS

In the process to prepare DIPE a feedstock comprising propene or a refinery $C_3$ hydrocarbon stream comprising olefins and paraffins, i.e., propene and propane, is contacted at elevated pressure with an acidic catalyst and water as a reactant to hydrate propene to form isopropanol (IPA) and etherify IPA to DIPE. Minor amounts of addition products of propene are also formed in the acidic catalyst environment, particularly hexenes and nonenes. On a per pass basis, the conversion of propene generally is about 60%, or between 50% and 70%. The effluent from the hydration and etherification zone is conventionally passed to a fractionator wherein a bottom stream is separated containing IPA and DIPE and an overhead stream that contains the unreacted hydrocarbons comprising propene and propane, if an olefin and paraffin feedstock has been used. The $C_3$ stream, typically containing both propene and propane, can be recompressed and recycled to the pressurized DIPE reactor. Since the recycle stream is rich in propane the DIPE feedstock stream pressure is increased in order to maintain the partial pressure of propene in the reactor. To avoid this, the recycle stream may be fractionated to purify propene recycle. Conventionally, DIPE is recovered by distillation and/or extraction of the fractionator bottom stream. This recovery system also separates an IPA stream and a water stream. The IPA stream can be recycled to the etherification zone.

The operating conditions of the olefin hydration and etherification process are not especially critical and include a temperature of from about 60 to 450° C., preferably from about 130 to about 220° C. and most preferably from about 150 to about 200° C., a pressure of from about 100 (700 kPa) to about 3500 psi (24,500 kPa), preferably from about 500 (3500 kPa) to about 2000 psi (14,000 kPa), a water to olefin mole ratio of from about 0.1 to about 30, preferably from about 0.2 to about 15 and most preferably from about 0.3 to about 3.

The olefin hydration process can be carried out under dense phase, liquid phase, vapor phase or mixed vapor-liquid phase conditions in batch or continuous manner, preferably using a fixed bed reactor. A liquid hourly space velocity (LHSV) of from about 0.1 to about 20, preferably about 0.1-2, when operating continuously is suitable.

The catalyst employed in the olefin hydration and etherification operations is acidic resin catalyst such as sulfonated polystyrene. Also, shape-selective acidic zeolite catalyst can be used. In general, the useful catalysts include zeolites Y, Beta and MCM-22. MCM-22 is described in allowed patent application Ser. No. 456,702, filed Dec. 26, 1989 to Bell, et al., incorporated herein by reference. Preferred catalysts include Zeolite Beta and Zeolite Y.

Zeolite Beta is described in U.S. Reissue Pat. No. 28,341 (of original U.S. Pat. No. 3,308,069), to which reference is made for details of this catalyst.

Zeolite Y is described in U.S. Pat. No. 3,130,007, to which reference is made for details of this catalyst.

Referring to the Figure the process of the present invention is illustrated. The principal units of the process as shown in the Figure include a DIPE reaction section 110; a fractionator 120 employed for the separation of DIPE and higher boiling reaction products from unreacted $C_3$ hydrocarbons comprising propane and propene plus a small amount of water; a first or aqueous extraction section 130 for the countercurrent extraction of DIPE reaction products with water; a second extraction section 140 for the countercurrent extraction of the aqueous phase from the first extraction section; and a fractionator 150 for separating the organic phase from the second extractor 140. The $C_3$ propane/propene feed to the process is used as the extracting media in the second extraction section 140.

With the second extraction section 140 operating at a temperature between about 21° C. and 121° C., but preferably between about 30° C. and 110° C., or at least between about 30° C. and 80° C. greater than the temperature of the first extraction zone, the $C_3$ hydrocarbon feed 142 is passed to the second extraction stage 140 countercurrent to the flow of aqueous isopropanol stream 132 from first extraction stage 130. The organic phase 144 from section 140, comprising principally propane, propene, IPA and a minor portion of water from stream 132 is passed to the fractionator 150 for further separation of the IPA/water components. The overhead stream 152 containing $C_3$ hydrocarbons rich in propene, IPA and some water sufficient to carry out the DIPE reaction is pumped to the DIPE reactor section 110 while the aqueous phase 146 from stage 140 comprising IPA and a major amount of the water from stream 132 is recycled to the first extraction stage 130. In the DIPE reactor 110 at a pressure of about 1500 psig (10,500 kPa) and about 320° F. (160° C.) the propene reacts with water to produce IPA and DIPE at a conversion of about 57%. The reaction products exit the reactor as an effluent 112 at a temperature of about 340° F. (171° C. and are cooled 114 to about 150° F. (66° C.). In the first stage extractor 13 the products are extracted with water from a feed water stream 134 as well as the recycle stream 148 at a temperature at least 3° C. below the operating temperature of the second stage extractor 140. The temperature of the first extraction zone is between about 20° C. and 80° C. at a pressure above 1750 kPa. Preferably, the temperature of the first stage extraction zone is between about 30° C. and 45° C. The aqueous phase from extractor section 130 is passed 132 to the second stage extractor as previously described. The organic phase containing DIPE and unreacted $C_3$ hydrocarbons is passed 136 to the splitter 120. In the splitter any entrained water is separated and the dry DIPE product is separated as a bottom stream 122. The overhead stream 126 comprises unreacted $C_3$ hydrocarbons. A portion of the 126 stream can be recycled to the second stage reactor section 140 in combination with the $C_3$ hydrocarbon stream 142.

Significantly, the extraction of aqueous isopropanol with $C_3$ hydrocarbon feed in the second stage extraction step described above can be carried out in a single stage or in multiple stages with the multiple stage process achieving an IPA recovery exceeding 50% of the IPA feed.

In addition to achieving a significant reduction in the size and energy consumption of distillation towers used to separate isopropanol and water in the DIPE process, the process configuration eliminates other vessels now employed in the art. Splitter 120 in the Figure eliminates the need for a separate dewatering step for DIPE while also serving to purge unreacted $C_3$ hydrocarbons. Water contained in the organic phase from the first extractor is removed in the splitter to produce dry DIPE. Furthermore, water washing the DIPE reactor effluent removes IPA from the organic phase containing DIPE and $C_3$'s. Water washing, in general, reduces the level of oxygenates in the organic phase and thereby reduces the amount of chemical species which can act as catalyst poisons in alkylation reaction. As a result, $C_3$'s leaving the recovery section can be sent directly to an alkylation unit to alkylate unconverted propene with isobutane by techniques well known in the art. The resultant once-thru DIPE process can show superior economics. Another advantage accrues from the utilization of the $C_3$ feedstream in countercurrent extraction with aqueous IPA. During this step impurities and catalyst poisons, particularly nitrogen compounds, are advantageously removed from the $C_3$ stream thereby eliminating the need for prior treatment of the $C_3$ stream as conventionally practiced to protect the etherification catalyst.

While the instant invention has been described by specific examples and embodiments, there is no intent to limit the inventive concept except as set forth in the following claims.

What is claimed is:

1. A process for the production of diisopropyl ether comprising;
   (a) contacting a feedstream comprising $C_3$ hydrocarbons rich in propene, isopropanol and water with acidic olefin hydration and etherification catalyst under etherification conditions at elevated pressure in an etherification zone to produce an effluent stream containing diisopropyl ether, isopropanol, unreacted water, unreacted $C_3$ hydrocarbons and higher olefinic hydrocarbons;
   (b) extracting said effluent stream with water in a first extraction zone to produce a first organic phase comprising diisopropyl ether and unreacted $C_3$ hydrocarbons and a first aqueous phase comprising isopropanol and water;
   (c) extracting said first aqueous phase with fresh $C_3$ hydrocarbon feedstock rich in propene in a second extraction zone to produce a second aqueous phase containing a minor portion of said first aqueous phase isopropanol and second extraction organic phase comprising a major portion of said isopropanol, said fresh $C_3$ hydrocarbons and water;
   (d) recycling said second aqueous phase to said first extraction zone;
   (e) distilling said second extraction organic phase in a fractionator to provide a bottom stream comprising water and an overhead stream comprising step (a) feedstream.

2. The process of claim 1 including the further step of separating said first organic phase in a splitter to produce an overhead stream comprising said unreacted $C_3$ hydrocarbons and a bottom stream comprising dry diisopropyl ether.

3. The process of claim 2 wherein a portion of said overhead stream is recycled to said second extraction zone.

4. The process of claim 1 wherein the temperature of said first extraction zone is between about 20° C. and 80° C. at a pressure above 1750 kPa.

5. The process of claim 4 wherein said temperature is between about 26° C. and 55° C.

6. The process of claim 1 wherein the temperature of said second extraction zone is at least 3° C. greater than the temperature of said first extraction zone.

7. The process of claim 1 wherein the temperature of said second extraction zone is between about 30° C. and 80° C. greater than the temperature of said first extraction zone.

8. In the process for the production of diisopropyl ether comprising contacting a $C_3$ hydrocarbon feedstream containing propene and water with acidic catalyst in a hydration and etherification zone under etherification conditions at elevated pressure to produce an effluent stream containing diisopropyl ether, isopropanol, unreacted $C_3$ hydrocarbons and water, the improvement which comprises:

extracting said effluent with water in a first extraction zone to produce an organic phase containing diisopropyl ether and unreacted $C_3$ hydrocarbons and an aqueous phase containing isopropanol; extracting said aqueous phase in a second extraction zone with fresh $C_3$ hydrocarbon feedstream; distilling the organic phase from said second extraction zone; and recovering a distillate comprising said $C_3$ feedstream containing propene and water.

9. The process of claim 8 including the further step of separating said first extraction zone organic phase in a splitter to produce an overhead stream comprising said unreacted $C_3$ hydrocarbons and a bottom stream comprising dry diisopropyl ether.

10. The process of claim 9 wherein a portion of said overhead stream is recycled to said second extraction zone.

11. The process of claim 8 wherein the temperature of said first extraction zone is between about 20° C. and 80° C.

12. The process of claim 11 wherein said temperature is between about 26° C. and 55° C.

13. The process of claim 8 wherein the temperature of said second extraction zone is at least 3° C. greater than the temperature of said first extraction zone.

14. The process of claim 8 wherein the temperature of said second extraction zone is between about 3° C. and 50° C. greater than the temperature of said first extraction zone.

* * * * *